United States Patent [19]
Norton

[11] Patent Number: 5,348,546
[45] Date of Patent: Sep. 20, 1994

[54] OSTOMY BAG WITH LIQUID-GAS SEPARATION DEVICE

[76] Inventor: Walter L. Norton, 208 State St., Newburgh, Ind. 47630

[21] Appl. No.: 65,341

[22] Filed: May 21, 1993

[51] Int. Cl.⁵ .................................................. A61F 5/44
[52] U.S. Cl. ...................................... 604/333; 604/332
[58] Field of Search ............................ 604/332–345, 604/379

[56] References Cited

U.S. PATENT DOCUMENTS

| | | | |
|---|---|---|---|
| 3,804,091 | 4/1974 | Nolan et al. | 604/333 |
| 4,387,712 | 6/1983 | Briggs et al. | 604/333 |
| 4,411,659 | 10/1983 | Jensen et al. | |
| 4,490,145 | 12/1984 | Campbell . | |
| 4,723,951 | 2/1988 | Steer . | |
| 4,826,495 | 5/1989 | Petersen . | |
| 4,957,522 | 9/1990 | Brassell . | |
| 5,074,851 | 12/1991 | Plass et al. | |
| 5,085,652 | 2/1992 | Johnson et al. | |
| 5,092,858 | 3/1992 | Benson et al. | 604/319 |
| 5,116,139 | 5/1992 | Young et al. | |

FOREIGN PATENT DOCUMENTS 1119568 7/1968 United Kingdom ................ 604/332

Primary Examiner—Randall L. Green
Assistant Examiner—Rob Clarke
Attorney, Agent, or Firm—Lowe, Price, LeBlanc & Becker

[57] ABSTRACT

An ostomy bag having a liquid-gas separation device includes a separator disposed within a flexible film pouch used as an ostomy bag. The separator is made of an absorbent material to collect liquids and separate these components from any gas entering the ostomy bag through the stomal opening thereof. The separator is spaced from a filter incorporated in the ostomy bag to further enhance gas-liquid separation. The separator may be disposed in the bag in an attached or unattached configuration. A perforated wall may be included within the flexible film pouch to minimize clogging of the separator by solids so as to improve and gas-liquid separation.

13 Claims, 2 Drawing Sheets

FIG. 1 PRIOR ART
FIG. 2 PRIOR ART
FIG. 3a
FIG. 3b
FIG. 4
FIG. 5a
FIG. 5b
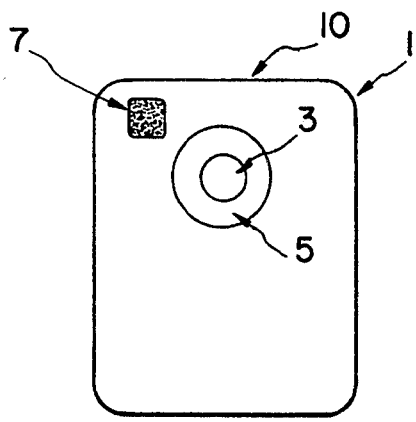
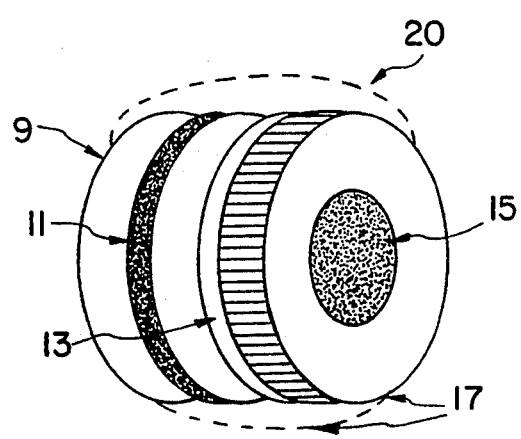
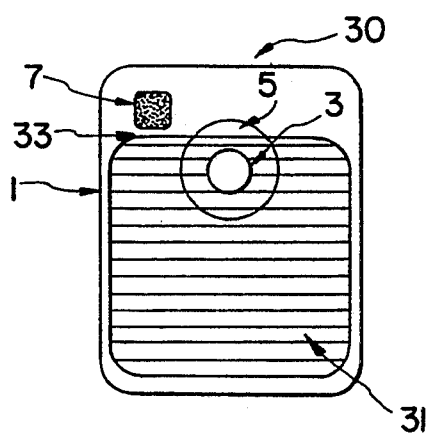
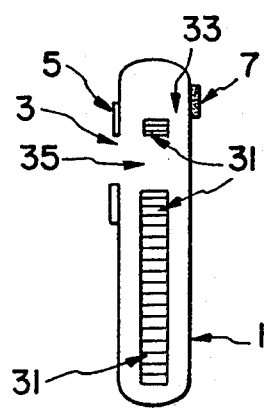
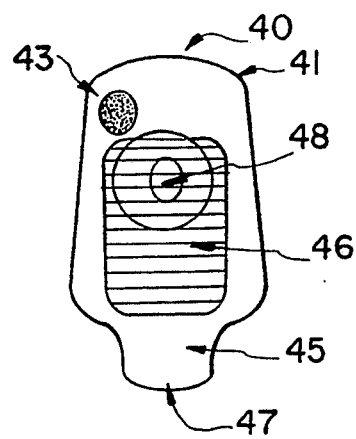
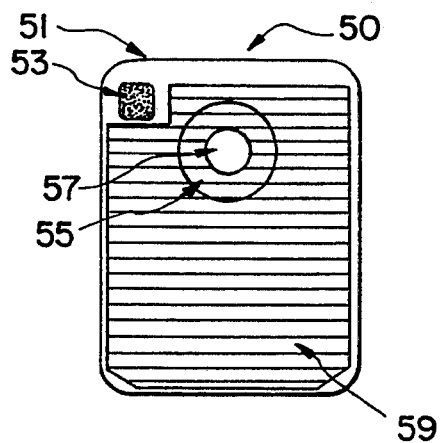
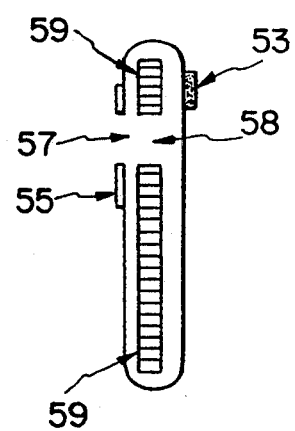

OSTOMY BAG WITH LIQUID-GAS SEPARATION DEVICE

FIELD OF THE INVENTION

The present invention relates to ostomy bags and, in particular, ostomy bags using deodorizing gas filters which include a liquid-gas separation device within the bag to prolong bag use.

BACKGROUND ART

In the prior art, it is known to provide colostomy and ileostomy patients with a waterproof, odorproof container or pouch to collect their intestinal discharge from surgically created stoma. Typically, these containers comprise a flat, flexible plastic bag, with an opening positioned over the patient's stoma. The bag is attached to the peri-stomal skin by an adhesive. FIG. 1 shows a typical ostomy bag designated by the reference numeral 10 and including a plastic film pouch 1, stomal opening 3, and an adhesive skin barrier 5 for attachment to a patient.

In some types of prior art bags, the bags were air tight which caused problems if a patient produced moderate or large amounts of bowel gas. This bowel gas can develop into a large bulge over the abdomen which can be embarrassing and uncomfortable to a user. In addition, and as additional gas accumulates, pressure within the bag rises causing the skin-adhesive-bag interface to separate, leading to external leakage.

To overcome these problems, the prior art bags incorporate an odor absorbing gas filter 7 into the wall of the bag so that gas can be vented outside of the bag (see FIG. 1). These filter devices work well when the intestinal discharge is solid so that the filter remains dry. However, if the filter becomes wet, it will transmit liquid intestinal contents to the exterior of the bag causing soiling of clothes and/or skin. These types of filters also stop functioning as a filter when the filter media, usually charcoal, becomes wet through contact with liquid contained within the plastic bag.

As can be seen from FIG. 1, the filters are usually located at the upper end of the ostomy bag and depend on gravity for separation of solids from gas. Typically, the gas rises to and through the filter with the liquid and/or solid material flowing downwardly. However, this separation process is usually unsuccessful when more than a few cubic centimeters of liquid are produced. The bag is constructed to have a generally flat profile and the bag sides are held in opposition by the design of the bag as well as compression of the bag between external clothing and the abdominal wall. The failure of the liquid and gas separation when more than a few cubic centimeters of liquid are produced is caused by the capillary action of the opposing sides of the flexible plastic bag. This results in the fluid within the bag being layered in a generally vertical direction, rather than collecting in the dependent or lower parts, resulting in liquid being drawn up through the filter to the outside of the bag. Under these conditions, the filter contributes to leakage by acting as a wick.

In view of the disadvantages and deficiencies of the prior art as explained above, a need has developed to provide an improved ostomy bag which overcomes the problems of liquid-gas separation and leakage of liquid through the bag filter.

The prior art has proposed collection pouches for use by ostomates to facilitate extended use of a pouch. U.S. Pat. No. 4,411,659 to Jensen teaches a barrier plastic film to shield the filter from exudate. However, this construction still fails to overcome the problem of fluid contacting and being drawn through the filter.

It is also known to use filtered stoma caps such as the one shown in exploded view depicted in FIG. 2 and generally designated as reference numeral 20. These stoma caps, one type manufactured by Convatec, include a perforated plastic cover 9, charcoal filter 11, and an absorbent backing 13 placed over the stomal opening 15 in the plastic film pouch 17. These devices function as a filter only and do not function well where more than a trace, e.g. 1 or 2 cc's, of intestinal contents is produced. Once the backing 13 becomes wet, the stoma filter has no capacity for solid or liquid storage. In fact, the backing actually draws liquid into the filter, rather than diverting it, further contributing to nonfunctionality.

In response to the disadvantages of the prior art as described above, the present invention provides an ostomy bag or pouch which can be worn for an extended period of time prior to changing through improved gas-liquid separation.

SUMMARY OF THE INVENTION

It is accordingly a first object of the present invention to provide an improved ostomy bag which permits bag use over an extended period of time.

It is another object of the present invention to provide an ostomy bag having a liquid-gas separation device therewith to permit gas free of contaminating liquids to exit the bag via a filter.

It is a still further object of the present invention to provide a liquid-gas separation device for use with existing ostomy bags or manufactured as a component thereof.

Other objects and advantages will be apparent as the description of the invention proceeds.

In satisfaction of the foregoing objects and advantages, there is provided by the present invention an ostomy bag comprising a flexible film pouch forming a lumen therein. The flexible film pouch includes a stomal opening through one wall thereof and a filter means for venting gases entering the flexible film pouch through the stomal opening. Also provided is a liquid-gas separator device arranged within the lumen and being spaced from and separate from the filter. In this arrangement, the space between the filter and opposing wall surface of the flexible film pouch is unobstructed. The liquid-gas separator is made of an absorbent material capable of absorbing liquids entering the lumen through the stomal opening. The absorbent material collects liquids, separating liquids from gas so as to maintain the filter in a functional mode.

The separator may be free standing in the lumen of the film pouch or attached to one wall thereof by an adhesive or the like. The separator may be sized and arranged in the lumen to cover the stomal opening or, alternatively, be sized and/or arranged such that the stomal opening is unobstructed.

The present invention also provides a method of separating gas and liquid in an ostomy bag having a stomal opening for receiving gas and liquid from a patient and a filter for venting the gas. The method comprises the steps of providing a separator made of an absorbent material, the separator placed in the lumen of an ostomy bag such that the separator is spaced from and separate from the filter. The ostomy bag is then attached to a patient to receive liquids, solids or gases therefrom. After attachment, liquids are collected in the ostomy bag and separated from the gases by contact with the absorbent material. Gases are then vented through the filter.

BRIEF DESCRIPTION OF DRAWINGS

Reference is now made to the drawings accompanying the invention wherein:

FIG. 1 is schematic view of a prior art ostomy bag;

FIG. 2 is an exploded view of a prior art stoma cap;

FIG. 3a is a schematic view of a first embodiment of the present invention showing the gas-liquid separation device in a standard ostomy bag; FIG. 3b is a cross sectional view of the first embodiment;

FIG. 4 is a second embodiment of the present invention showing an alternative liquid-gas separation device in a prior art ostomy bag;

FIG. 5a shows a third embodiment of the present invention illustrating the liquid-gas separation device in side and FIG. 5b shows cross-sectional schematics of the third embodiment of the inventive ostomy bag;

DESCRIPTION OF THE PREFERRED EMBODIMENTS

Figure 6A:
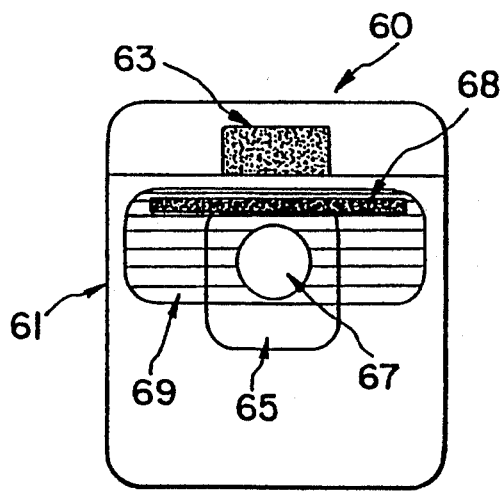
FIG. 6a is a schematic side and FIG. 6b is sectional view of a fourth embodiment of the invention.

The present invention solves the problems discussed above in prior art ostomy bags by providing a liquid-gas separation device in the bag. This liquid-gas separation device or separator is placed inside the ostomy bag so that fluid comes into contact with the separator before contacting the filter. With this configuration, the separator permits the gas phase within the bag to exit the filter free of contaminating liquids. The separator also greatly prolongs the time a pouch can be worn before it must be changed because of liquid contamination of the filter.

In prior art designs, filters can become wet with as little as 5 cc's of liquid, sometimes within only a few minutes of application. However, most normally functioning colostomies with adequate bowel training will produce from a few to approximately 30 cc's of liquid per 24 hours. When a patient experiences an unexpected heavy liquid flow such as an attack of diarrhea, prior art ostomy bags rapidly become non-functional or leak.

The inventive ostomy bag with the liquid-gas separator is capable of storing liquids and solids and providing a safety reservoir in the event of unexpected heavy liquid flow. This safety reservoir allows a user time to switch to a new ostomy bag or a non-filtered pouch before leakage through the filter occurs.

The inventive ostomy bag also contributes to improved filter performance by maintaining a separation between the separator and the filter. This separation maintains the filter in a dry state to permit proper odor absorption.

With reference now to FIG. 3, a first embodiment of the present invention is generally designated by the reference numeral 30 and is seen to include a plastic film pouch 1 having a stomal opening 3 therein. The stomal opening 3 is surrounded by an adhesive skin barrier 5 for attachment of the plastic film pouch 1 to a user. Mounted in the plastic film pouch is a filter 7 which vents gas outside of the plastic film pouch 1. Arranged inside the pouch is a separator 31 which is spaced from the filter 7 as indicated by reference numeral 33. In this embodiment, the separator 31 includes an opening 35 aligned with the stomal opening 33. Although an adhesive skin barrier is shown as an attachment device, other known attachment devices including two piece bag designs may be used to secure the bag to a patient.

The separator 31 can be any absorbent material capable of retaining liquids in the ostomy bag. Preferred materials are non-toxic materials which are known to be safe when in contact with human skin or mucosa. Examples of these materials include cotton-containing materials such as cotton fiber or woven cotton string, such as those used in sanitary tampons or pads. Alternatively, absorbent paper products such as used in absorbent tissue, filter paper, blotters or paper towels may be used.

The separator can also have varying degrees of rigidity depending on the manner of placement or attachment in the plastic film pouch. For example, the separator may be made of a fibrous material with a degree of rigidity to permit an upstanding configuration, for example, something similar to one or more layers of paper toweling. Alternatively, the separator can have a low level of rigidity and a low co-efficient of friction, e.g., one or more layers of a satin-like material. Separators having lower levels of rigidity may require additional means of support when placed in the plastic film pouch as will be described in hereinafter.

FIG. 4 shows a second embodiment of the present invention generally designated by the reference numeral 40 and seen to include a drainable plastic film pouch 41 having a replaceable filter 43. The plastic film pouch 41 includes a drain portion 45 and drain opening 47. The drain opening 47 is normally closed using a plastic clip (not shown) or the like.

Disposed within the plastic film pouch 41 is a separator 46. The separator 46 is arranged to cover the stomal opening 48.

It should be understood that the separator for use with a plastic film pouch may be utilized as an add-on to standard stoma pouches. In this manner, the separator can be inserted through the stomal opening of a closed bag such as the one depicted in FIG. 3. Alternatively, the separator can be inserted through the drain end of a drainable filter pouch such as the pouch depicted in FIG. 4. The separator may also be incorporated during manufacture of the bag so that it is ready for use when purchased.

FIG. 5 shows a third embodiment of the present invention, generally designated by the reference numeral 50. In this embodiment, a plastic film pouch 51 includes a filter 53, an adhesive skin barrier 55 and a stomal opening 57. An absorbent separator 59 is manufactured or cut to fit within the plastic film pouch 51. The separator 59 includes a through opening 58 designed to align with the stomal opening 57 in the film pouch 51. In this embodiment, the separator 59 is sized to coincide with the overall shape of the film pouch 51 except for the area in the region of the filter 53. This design provides a maximum amount of absorbent material to provide adequate separation between liquids and gases venting through the filter 53. Separation of the filter 53 and separator 59 maintains the filter in a dry state and spaced from any effluent in the plastic film pouch 51.

Figure 6B:
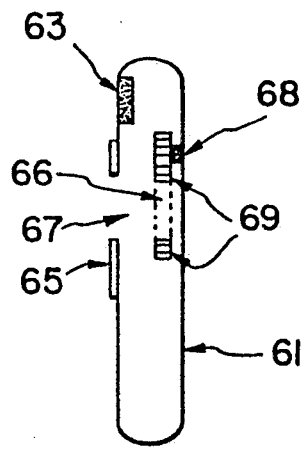

FIG. 6 shows a fourth embodiment of the invention wherein anchors or other retaining means are utilized to hold the absorbent separator in place. This embodiment is generally designated by the reference numeral 60 and is seen to include a plastic film pouch 61, filter 63, adhesive skin barrier 65 or other attachment method and stomal opening 67. The separator 69 is mounted within the plastic film pouch 61 by an anchor 68. Although one anchor is depicted, more than one anchor may be utilized depending on the bag configuration and replacement of the absorbent separator. The anchor 68 may be any type capable of retaining the absorbent separator material in position within the plastic film pouch 61. For example, the anchor(s) may be a non-toxic adhesive. The separator 69 also includes a through opening 66 which aligns with the stomal opening 67.

As shown in the embodiments depicted in FIGS. 5 and 6, the separator may be custom fit to the plastic film pouch shape depending on the particular intended use. In FIG. 5, the separator may be placed freely within the lumen of the plastic film pouch 51 without need for attachment. In FIG. 6, the truncated configuration of the separator 69 requires use of an adhesive or other anchor to retain the separator in place within the pouch.

Figure 7A:
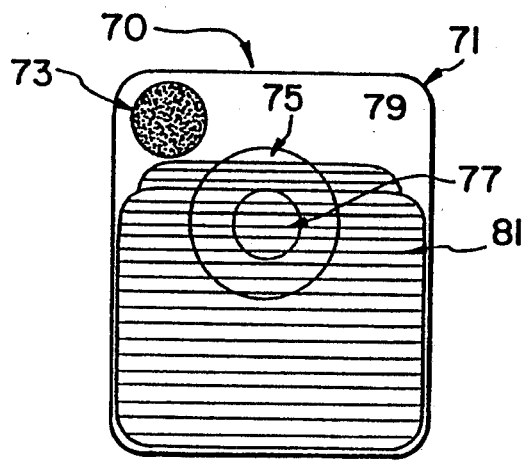
FIG. 7a is a schematic side and FIG. 7b is sectional view of a fifth embodiment of the present invention.
Figure 7B:
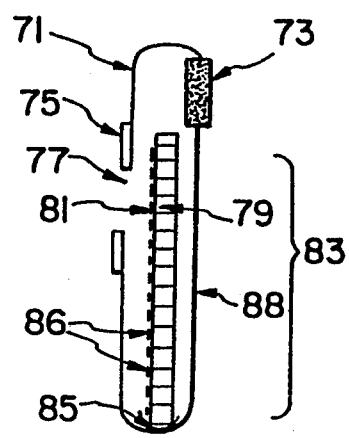

Under certain situations, formed bowel contents may absorb or cling to the separator. This adsorption may inhibit flow of additional solid material to the dependent or lower part of the ostomy bag. FIG. 7 depicts an embodiment which minimizes the absorption of solid or formed bowel contents to the separator. This embodiment is generally designated by the reference numeral 70 and includes a plastic film pouch 71, filter 73, adhesive skin barrier 75 and stomal opening 77. Arranged within the plastic film pouch 71 is a perforated wall 81. The wall 81 may be attached at reference numeral 85 to the plastic film pouch 71 and extend upwardly beyond the stomal opening 77. The wall 81 forms a pocket 83 designed to receive the separator 79. With this configuration, the wall 81 minimizes or prevents contact between solid material entering the stomal opening and the separator 79. The solid material flows to the dependent part of the bag. The perforations 86 in the wall permit fluid flow therethrough for gas-liquid separation and fluid absorption by the separator 79.

Figure 8:
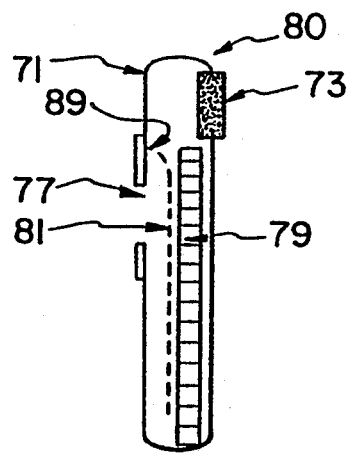
FIG. 8 is a schematic sectional view of an alternative design for the location and attachment of the perforated film barrier described in FIG. 7.

FIG. 8 shows an alternative location of a perforated film barrier curtain 81 attached to film pouch 71 above the stoma opening 77 which diverts the effluent stream downward while maintaining a path for liquid and gas to access the separator 79 and gas filter 73.

The perforated wall 81, although shown attached to the film pouch 71 may be merely inserted therein to provide the barrier layer against solid material. When not attached, the perforated wall 81 should have sufficient rigidity to remain vertically upstanding during use. Alternatively, the perforated wall may be attached to the separator.

The separator may be configured within the lumen of the plastic film pouch so as to cover the stoma or leave the stomal opening unobstructed. If the separator is made so as to cover the stomal opening, it should be understood that any attachment used to retain the separator to the inside surface of the plastic film pouch is preferably made on the anti-abdominal pouch wall. For example, and with reference to FIG. 7, wall 88 corresponds to the anti-abdominal wall. If the separator does not cover the stomal opening, it may be attached to either of the pouch walls.

The inventive liquid-gas separator may be used in any known container designed to collect human body fluids such as intestinal discharge. This includes containers with or without gas venting filtering devices. However, a preferred use of the inventive liquid-gas separator includes ostomy bag with filter devices therein.

As such, an invention has been disclosed in terms of preferred embodiments thereof which fulfills each and every one of the objects of the present invention as set forth hereinabove and provides a new and improved ostomy bag.

Of course, various changes, modifications and alterations from the teachings of the present invention may be contemplated by those skilled in the art without departing from the intended spirit and scope thereof. Accordingly, it is intended that the present invention only be limited by the terms of the appended claims.

I claim:

1. An ostomy bag comprising:
   a) a flexible film pouch forming a lumen therein, said flexible film pouch including a stomal opening through one wall thereof and a filter for venting gases entering said flexible film pouch through said stomal opening, said filter arranged in a first plane; and
   b) a liquid-gas separator arranged within said lumen in a second plane generally parallel to said first plane, at least a portion thereof laterally positioned between said filter and said stomal opening, said filter being spaced laterally from said liquid-gas separator in a direction parallel to said first plane so that said filter and said liquid-gas separator lack coincidence in a direction generally perpendicular to said first plane, said liquid-gas separator made of an absorbent material for absorbing liquids entering said lumen through said stomal opening and separating said liquids from said gas wherein said lack of coincidence facilitates simultaneous venting of gases and storage of high volumes of liquids and said portion defeats capillary action of fluid toward said filter.

2. The ostomy bag of claim 1 wherein said absorbent material is selected from the group consisting of cotton, cotton-containing products, and absorbent paper products.

3. The ostomy bag of claim 1 wherein said separator is arranged within said lumen to cover said stomal opening.

4. The ostomy bag of claim 1 wherein said separator has a through opening and is arranged in said lumen so that said through opening aligns with said stomal opening.

5. The ostomy bag of claim 1 further comprising a perforated barrier wall disposed in said lumen so that at least a portion thereof is between said stomal opening and said separator.

6. The ostomy bag of claim 5 wherein said perforated barrier wall is freestanding in said lumen.

7. The ostomy bag of claim 5 wherein said perforated barrier wall is attached to at least a portion of said flexible film pouch.

8. The ostomy bag of claim 1 wherein said separator is freestanding in said lumen.

9. The ostomy bag of claim 1 wherein said separator is adhesively mounted to a wall of said flexible film pouch.

10. The ostomy bag of claim 1 wherein said separator is sized and arranged in said lumen so that said stomal opening is unobstructed.

11. A method of separating gas and liquid in an ostomy bag having a stomal opening for receiving said gas and liquid and a filter arranged in a first plane for venting said gas comprising the steps of:
   a) providing a separator made of an absorbent material in a lumen of said ostomy bag, said separator arranged in said ostomy bag in a second plane parallel to said first plane, at least a portion thereof laterally positioned between said stomal opening and said filter, said filter being spaced laterally from said separator in a direction parallel to said first plane so that said filter and said separator lack coincidence in a direction perpendicular to said first plane;
   b) attaching said ostomy bag to a patient to receive liquids, solids and gases from said patient;
   c) collecting liquids in said ostomy bag and separating said liquids from said gases by said absorbent material contacting said liquids;
   d) defeating capillary action of fluids in said ostomy bag by said lateral positioning of said portion of said separator between said stomal opening and said filter; and
   e) venting said gases through said filter.

12. The method of claim 11 wherein a cotton-containing material or an absorbent paper material is provided as said absorbent material.

13. The method of claim 11 further comprising the step of:
   i) providing a perforated barrier wall in said ostomy bag, a portion of said perforated barrier wall arranged between said stomal opening and said separator; and
   ii) separating said solids from said separator using said perforated barrier wall while liquid passes through said perforated barrier wall for absorption by said separator.

* * * * *